United States Patent [19]

Ritchey

[11] Patent Number: 4,560,549

[45] Date of Patent: Dec. 24, 1985

[54] METHOD OF RELIEVING PAIN AND INFLAMMATORY CONDITIONS EMPLOYING SUBSTITUTED SALICYLAMIDES

[75] Inventor: Thomas W. Ritchey, Norwood, N.J.

[73] Assignee: Lever Brothers Company, New York, N.Y.

[21] Appl. No.: 525,916

[22] Filed: Aug. 24, 1983

[51] Int. Cl.[4] .................. A61K 9/22; A61K 9/52; A61K 9/70
[52] U.S. Cl. ..................................... 424/18; 424/28
[58] Field of Search .................................. 424/28, 18

[56] References Cited

U.S. PATENT DOCUMENTS

| | | | |
|---|---|---|---|
| 2,975,097 | 3/1961 | Modderno | 424/45 |
| 3,027,301 | 3/1962 | Freedman | 424/324 |
| 3,317,583 | 5/1967 | Hsi | 260/465 |
| 3,917,617 | 11/1975 | Razdan | 260/239 B |
| 4,008,274 | 2/1977 | Sawatari et al. | 260/559 S |
| 4,091,097 | 5/1978 | Umezawa et al. | 424/230 |
| 4,199,576 | 4/1980 | Reller et al. | 424/230 |
| 4,275,059 | 6/1981 | Flora et al. | 424/204 |
| 4,287,191 | 9/1981 | Coburn | 424/230 |
| 4,358,443 | 11/1982 | Coburn et al. | 424/230 |

FOREIGN PATENT DOCUMENTS

| | | |
|---|---|---|
| 884977 | 8/1980 | Belgium . |
| 0058009 | 1/1982 | European Pat. Off. . |
| 2336526 | 2/1975 | Fed. Rep. of Germany . |
| 1094578 | 5/1955 | France . |
| 8118M | 12/1965 | France . |
| 6677M | 2/1969 | France . |
| 112255 | 5/1975 | German Democratic Rep. . |
| 50-129738 | 10/1975 | Japan . |
| 1427112 | 3/1976 | United Kingdom . |
| 1378618 | 12/1976 | United Kingdom . |

OTHER PUBLICATIONS

Batista, A. J., "Salicylanilides: Design, Synthesis, and in Vitro Evaluation as Inhibitors of Dental Plaque-Forming Microorganisms", PhD Dissertation, State University of New York at Buffalo, 1980.
Derwent Publications Accession No. 81692Y/46 relating to Japanese Patent Document No. 37488.
Chemical Abstract No. 3727B.
Chemical Abstract No. 95:168822e.
Chemical Abstract No. 98:16432b.
Chemical Abstract No. 88062h.
Chemical Abstract No.: 140260d.
Chemical Abstract No.: 84:4938u.
Chemical Abstract No.: 192869y.
Chemical Abstract No.: 85:142860j.
Chemical Abstract No.: 88:58568z.
Chemical Abstract No.: 93:150019x.
Chemical Abstract No.: 84:58969y.
Chemical Abstract No.: 43383h.
Chemical Abstract No.: 84:4689p.

Primary Examiner—Stanley J. Friedman
Attorney, Agent, or Firm—Lynne Darcy; James J Farrell

[57] ABSTRACT

A topically and systemically administered anti-inflammatory composition for human and for veterinary consumption which comprises compounds of the general formula:

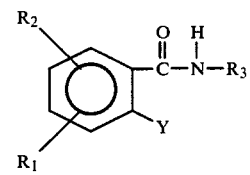

wherein $R_1$, $R_2$ and $R_3$ are defined hydrocarbon attachments and Y is —OH or a phenolic ester group derived from the reaction of such —OH group with a carboxylic acid halide or anhydride.

In typical compounds covered by said general formula
(a) $R_1$ is H, $R_2$ is 5,n-octanoyl, Y is hydroxy and $R_3$ is p-trifluoromethylphenyl;
(b) $R_1$ is H, $R_2$ is 5,n-decanoyl, Y is hydroxy and $R_3$ is benzothiazol-2-yl and
(c) $R_1$ is H, $R_2$ is 5,n-decanoyl, Y is acryloyloxy and $R_3$ is p-nitrophenyl.

The resulting compositions take the form of ointments, solid sticks, tablets, capsules, injectable solutions and suspensions, ear drops, eye drops, nose drops, douches, suppositories, enemas, liniments, gels, lotions, shampoos, soaps, creams, solutions, aerosols, pads, plasters, bandages, dressings and catamenial and non-catamenial tampons. The compositions are useful in relieving pain or inflammation as well as microbial infections in mammals when applied topically to the skin or affected organs or when administered systemically.

45 Claims, No Drawings

METHOD OF RELIEVING PAIN AND INFLAMMATORY CONDITIONS EMPLOYING SUBSTITUTED SALICYLAMIDES

This invention relates to the novel use of certain secondary amido compounds including certain salicylanilides as systemic analgesic agents and also for topical application as anti-inflammatory compositions.

A group of compounds which are known to possess analgesic properties are derivatives of salicylic acid, in particular acetylsalicylic acid which is more commonly known as aspirin. Aspirin is a widely known and extensively used orally administered antipyretic analgesic. Methyl salicylate, which is closely related thereto is the active ingredient of oil of wintergreen (*Gaultheria procumbens*). Oil of wintergreen is used as a topical analgesic. However, it is interesting to note in this regard that although topically applied, such use is contraindicated by the fact that oil of wintergreen is a mild skin irritant. It is useful for the treatment of sore muscles and not for the relief of skin inflammation per se.

A number of different amido compounds having anti-inflammatory activity have been reported in "Nature", 222, 275:1969; "J. Med. Chem.", 14, 973 (1971); "J. Med. Chem.", 14, 1171 (1971), "J. Med. Chem.", 15, 551 (1972); "J. Med. Chem.", 15, 848 (1972) and in "J. Med. Chem." 16, 493 (1973).

U.S. Pat. No. 3,917,617 discloses analgesic, antibacterial, antifungal and antidepressant properties having resorcinol derivatives of the formula:

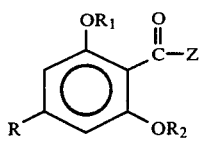

wherein R represents an alkyl group having 1 to 20 carbon atoms, an arylalkyl group, or a cycloalkyl-lower alkyl group;

$R_1$ and $R_2$ represent hydrogen or the same or different lower alkyl or lower alkanoyl groups; and Z represents —$NH_2$, —$NHR_3$, —$NR_3R_4$, or

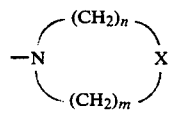

where $R_3$ is lower alkyl or phenyl-lower alkyl, $R_4$ is lower alkyl or phenyl-lower alkyl, m is an integer from 0 to 6, n is an integer from 0 to 6, m+n is an integer from 3 to 6, and X is $CH_2$, $CHR_3$, O, S, or $NR_3$.

U.S. Pat. No. 3,027,301 discloses inter alia as useful wound healing agents hydroxypropylsalicylamides of the formula:

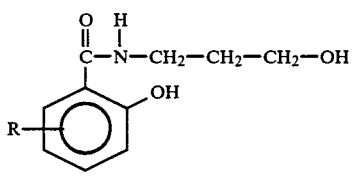

wherein R is a member of the group consisting of hydrogen, hydroxyl, methyl, chlorine, and phenyl, and a pharmaceutical carrier.

French Pat. No. 1,094,578 discloses the use as antiseptics halogenated salicylanilides of the formula:

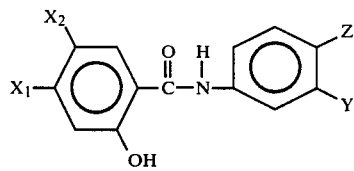

wherein $X_1$ and $X_2$ are a hydrogen or a halogen atom or a methyl group; Y is a hydrogen or a halogen atom or a trifluoromethyl group and Z is a hydrogen or a halogen atom.

U.S. Pat. No. 4,287,191 describes compositions effective as antiseptics against a wide range of microorganisms, especially those prevalent in dental plaque comprising novel 5-acyl-salicylanilides including compounds of this invention, of the formula:

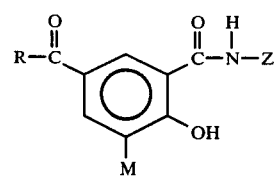

In the above formula, Z is a substituted phenyl ring of from 6 to 30 carbon atoms including substituents, R is a substituted or unsubstituted alkyl or phenyl group of from 2 to 30 carbon atoms including substituents and M is a radical selected from the group consisting of —C≡N, —F, —$NO_2$, —H, lower alkyl or lower haloalkyl.

Batista, A. J., "Salicylanilides: Design, Synthesis, and In Vitro Evaluation as Inhibitors of Dental Plaque-Forming Microorganisms", Ph.D. Dissertation, State University of New York at Buffalo, 1980 discloses the synthesis of and microbiocidal properties of substituted salicylic acids, salicylates and salicylanilides, including compounds employed in this invention.

It is an object of the present invention to provide methods for the relief of pain and inflammation in human and in veterinary subjects.

It is a further object of the present invention to provide compositions for topical and for systemic application in such context.

It is a further object of the present invention to provide such compositions of high effectiveness and low toxicity.

It is a further object of the present invention to provide such compositions in a wide variety of administration vehicles to enable topical and systemic application thereof in a correspondingly wide range of applications.

These and other objects will become apparent on further reading of this specification.

In a composition aspect, this invention relates to anti-inflammatory compositions which comprise, in admixture with a pharmaceutically acceptable carrier vehicle, an anti-inflammatorily effective amount of a compound of the formula:

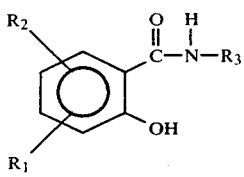

Formula I bearing on the benzene ring at least one lipophilic substituent which imparts to the compound a distribution coefficient in octanol/water of about 4.5 to about 10 wherein the substituents —$R_1$ and —$R_2$ are —H, normal or branched chain or cyclic or fused ring polycyclic or non-fused ring polycyclic, alkyl, alkenyl, alkynyl, aryl or heteroaryl groups optionally containing further substituents thereon, said —$R_1$ and —$R_2$ substituents comprising up to about 30 carbon atoms when taken together either attached directly to the phenyl ring or through a

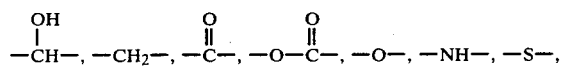

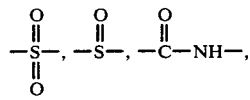

—NH—CH$_2$— and

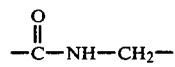

group with the proviso that at least one of —$R_1$ and —$R_2$ is other than —H; and wherein —$R_3$ is selected from the group consisting of thiazol-2-yl, benzothiazol-2-yl and $R_4$-substituted phenyl, i.e., of the formula:

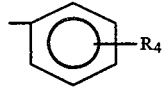

wherein —$R_4$ is selected from the group consisting of —CH$_2$R$_5$, —OH, —COOH, the tautomeric pair

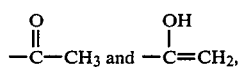

—CH$_2$COOH, —COOCH$_3$, —COOC$_2$H$_5$, —CH$_2$COOCH$_3$, —CH$_2$COOC$_2$H$_5$, —NO$_2$, CX$_1$X$_2$X$_3$ wherein X$_1$, X$_2$ and X$_3$ are halogen atoms, which can all be different halogen atoms or wherein two or more halogen atoms are alike, wherein —R$_5$ is H, alkyl, cycloalkyl, or their unsaturated counterparts, aryl or heteroaryl comprising up to a total of about 24 carbon atoms. Alternatively, —R$_3$ may simply be any aryl or heteroaryl group or a secondary amido ligand —CH$_2$—R$_6$ wherein —R$_6$ is —H or an attachment of up to 24 carbon atoms of the same description as —R$_1$ or —R$_2$ involving the same linking groups between itself and the methylene group directly attached to the amido nitrogen atom.

In the Formula I shown above, alkyl can be straight or branched chain, e.g., n-octyl, n-decyl or tert-butyl; cycloalkyl can be monocyclic, e.g.,

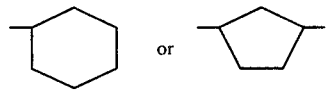

fused polycyclic, e.g.,

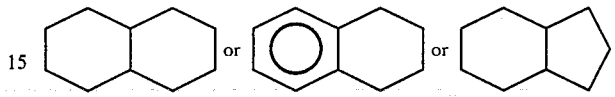

or non-fused polycyclic, e.g.,

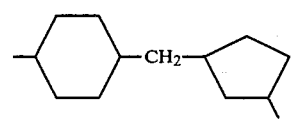

alkenyl can be, e.g., CH$_2$=CH$_2$—(CH$_2$)$_n$— where n is an integer or CH$_3$—(CH$_2$)$_n$CH=CH(CH$_2$)$_m$— where n and m are each either zero or an integer it being understood that one or more double bonds may be included in the formula; alkynyl can be, e.g., HC≡C— or CH$_3$(CH$_2$)$_n$— C≡C—(CH$_2$)$_m$— where m and n are each zero or an integer it being understood that one or more triple bonds may be included in the formula; aryl can be mono or polycyclic, e.g.,

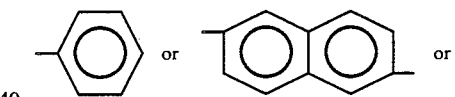

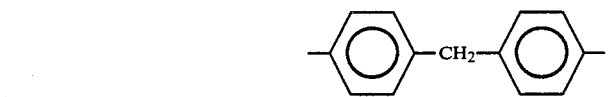

and heteroaryl can be mono or polycyclic and can contain 1,2,3 or more heteroatoms, e.g., N, O or S, e.g.,

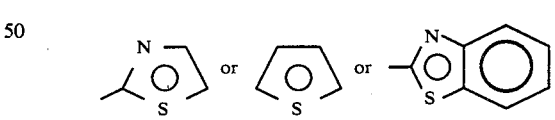

Each of the respective groups can bear one or more substituents such that —R$_1$ and —R$_2$ taken together contain collectively up to about 30 carbon atoms and —R$_3$ contains up to about 25 carbon atoms. It will therefore be understood that the examples given are only illustrative and not limitative of the invention.

In one method of use aspect, this invention relates to a method of alleviating pain in mammals, particularly human subjects by the systemic administration of a composition comprising a compound or compounds of Formula I.

In another method of use aspect, this invention relates to a method for treating dermatological inflammation and pain which comprises topical application of a composition comprising a compound or compounds of Formula I over areas of said dermatological inflammation in mammals, particulary human beings over a therapeutically effective length of time.

In yet another method of use aspect, this invention relates to a method of alleviating pain and inflammation in mammalian organs and body cavities such as the ear, eye, nose, vagina, anus and rectum.

The compounds of Formula I may be incorporated (without limitation) in petroleum jelly, lanolin, paraffin wax, alkanols and mixtures thereof as well as other comparable vehicles noted in the succeeding Examples. Alternative vehicles include, without limitation ointments, sticks, capsules and tablets, injection solutions or suspensions, other solutions, shampoos, soaps, creams, water, aerosol bases, medicated pads, medicated plasters, medicated bndages, medicated dressings, and medicated catamenial and non-catamenial tampons. Incorporation of the compounds of Formula I in suitable carriers also results in ear drops, eye drops, nasal drops, anal and vaginal suppositories, enemas and douches as well as liniments, gels and lotions. The foregoing general examples as well as the specific Examples noted below are illustrative and not limitative of this invention.

The medicated articles are placed in intimate contact with the affected organ or the medicated compositions applied to the affected skin, mucuous membrane or organ for a sufficient length of time to relieve pain with repeat applications as needed. By making such use of the compounds of Formula I, pain and inflammation in, e.g., the ear, eye, nose, anus and vagina or any other affected organ or cavity are relieved.

Topical application on the skin of the compounds of Formula I in the form e.g. of ointments, sticks, shampoos, soaps, creams, water and other solutions, aerosol bases, medicated pads, medicated plasters, medicated bandages, medicated dressings, liniments, gels and lotions results in the relief of skin inflammation and pain. The skin inflammation treated by this invention can be the result of various skin disorders such as eczema, psoriasis, seborrheic dermatitis, contact dermatitis, allergic dermatitis, reactions due to poison ivy, poison oak, stinging nettles, etc. Further included within the purview of this invention and illustrative but not limitative thereof are skin inflammation caused by tissue damage resulting from ultraviolet or other electromagnetic radiation including sunburns, insect and kindred bites and stings as well as thermal burns.

The preferred salicylamides of Formula I have an octanol/water distribution coefficient greater than 4.5 and the substituted moieties —$R_4$ in the phenyl ring of the secondary amido ligand (when the —$R_3$ ligand takes the form —$PhR_4$, Ph being a phenyl ring) have a combined overall electron withdrawing effect on said phenyl ring.

The term "distribution coefficient" of a composition as used herein is the $\log_{10}P$ where P is the ratio of the concentration of the composition in octanol to the concentration of the composition in water in a two phase octanol-water system. A distribution coefficient of, e.g., 5 therefore means that the ratio of the concentration of the compound in octanol to the concentration in water is $10^5$ or 100,000 to 1. The distribution coefficient is a measure of the lipophilic character of the compound. The preferred compounds of Formula I are lipophilic as indicated by a distribution coefficient of greater than about 4.5. The distribution coefficient is however usually less than 10.

The preferred compounds of Formula I are those of the structure shown below:

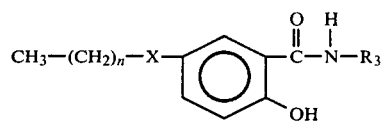

wherein n is an integer, preferably from 3 to 14, $R_3$ is as defined above and X is $$-\underset{\underset{\text{}}{\|}}{\overset{\text{O}}{\text{C}}}-$$

or a covalent bond joining the alkyl group to the phenyl ring. When —$R_3$ is an $R_4$— substituted benzene ring, $R_4$— preferably is para —$NO_2$, meta —$COOC_2H_5$ or meta or para —$CF_3$.

Of the preferred compounds, especially preferred are those wherein:

(a) n is 8, X is $$-\overset{\text{O}}{\underset{\|}{\text{C}}}-,$$

and —$R_3$ is a para-nitrophenyl, (hereinafter called AN-10), (b) n is 6, X is $$-\overset{\text{O}}{\underset{\|}{\text{C}}}-,$$

and —$R_3$ is a para-trifluoromethylphenyl (hereinafter called APCF3-8), (c) n is 6, X is $$-\overset{\text{O}}{\underset{\|}{\text{C}}}-$$

and —$R_3$ is a meta-trifluoromethylphenyl (hereinafter called AMCF3-8), (d) n is 5, X is a covalent bond and —$R_3$ is a para-nitrophenyl (hereinafter called SAN-6), (e) n is 3, X is a covalent bond and —$R_3$ is a meta-trifluoromethylphenyl (hereinafter called S-4-F), (f) n is 7, X is $$-\overset{\text{O}}{\underset{\|}{\text{C}}}-$$

and —$R_3$ is meta-carbethoxyphenyl (hereinafter called ACBXE-9), (g) n is 8, X is $$-\overset{\text{O}}{\underset{\|}{\text{C}}}-$$

and —$R_3$ is benzothiazol-2-yl (hereinafter called ABC-4), and (h) n is 14, X is and —$R_3$ is thiazol-2-yl (hereinafter called RV-19), (i) n is 8, X is

—$R_3$ is a para-nitrophenyl and the —OH group of Formula I is replaced with a $CH_2=CH-COO—$ group (hereinafter called acryloyl AN-10).

The salicylamides of Formula I have analgesic and anti-inflammatory activity. The preferred salicylamides have excellent analgesic properties and many of them exhibit low toxicity in mammals.

The salicylamides of the above formulae are as already noted above, also useful for relieving dermal inflammation. The treated dermal inflammation or painful condition is the result of disorders such as or due to eczema, psoriasis, seborrheic dermatitis, contact dermatitis, allergic dermatitis, reactions due to poison ivy, poison oak and stinging nettles, etc. and sunburns, thermal burns, other electromagnetic radiation burns, insect and kindred bites and stings. The foregoing list of disorders and conditions is only illustrative but not limitative of the invention.

Likewise, such compositions may be administered systemically to relieve pain at sites which are only reached or preferentially reached by analgesic compositions administered systemically. The term "systemic administration" as used herein includes oral administration, parenteral administration (including administration by way of intramuscular, subcutaneous, intraarticular and intravenous injections) and through body cavities such as the ear, nose, eye, vagina and anus.

It is understood that the use of compositions or articles containing the compounds of Formula I in the mucous membranes of e.g. the nose and vagina are a form of topical administration.

The method in accordance with the present invention for relieving dermal inflammation whether in human subjects or in veterinary applications comprises contacting the affected skin or organ with a salicylamide of Formula I suspended in a pharmaceutically acceptable carrier vehicle. Likewise, as already noted above, when it is therapeutically advantageous to do so, systemic administration of a compound of Formula I may be employed as a further method within the scope of this invention. Such a carrier vehicle constitutes a compatible spreadable base and may be one selected from the group consisting of petroleum jelly, lanolin, paraffin wax, alkanols and mixtures thereof. Further, non-limiting examples of compatible spreadable bases are described within the illustrative Examples included in this specification.

When a salicylamide of Formula I is suspended in a hard base such as paraffin wax, a stick for topical application to the affected areas is obtained. Likewise, when the carrier vehicle is a soft pasty substance like lanolin or petroleum jelly, an ointment suitable for dispensing from a collapsible tube is obtained. Advantageously, said compounds may be incorporated into solution, aerosol, cream, lotion, ointment, liniment, gel, shampoo, soap, suppository, or liquid bases to form solutions, aerosols, creams, lotions, ointments, liniments, gels, shampoos, soaps, suppositories (vaginal and anal), ear, eye, and nose drops, enemas, douches and injectable solutions and suspensions. Likewise, incorporation of such compositions in pads, plasters, bandages, dressings, catamenial and non-catamenial tampons results in medicated pads, medicated plasters, medicated bandages, medicated dressings and medicated tampons (catamenial and non-catamenial) all for use in the practice of this invention.

Very small concentrations of a salicylamide of Formula I in an acceptable carrier vehicle are effective, with concentrations of about 0.1 microgram to about 50 micrograms per milliliter of carrier vehicle being sufficient in most cases.

In topical applications of a salicylamide of Formula I, a very short contact time of e.g. 10 seconds may be sufficient. If necessary, the contact time is extended to about 24 hours. Also, if necessary, such topical application is repeated, as needed.

It is a further advantage of the invention that the analgesic nature of the salicylamides of Formula I, together with their low toxicity make their systemic use possible both in human subjects and in veterinary applications. The toxicity thereof as measured by the designation $LD_{50}$ has been found, in oral administration in rats to be about 2.0 g/kg. body weight. The comparable toxicity $LD_{50}$ for aspirin is about 1.75 g/kg. body weight. Because of their low toxicity, in addition to topical application, they may also be administered orally or parenterally. Such parenteral application may take the form (a) of ear, eye and nasal drops (all in suitable carrier vehicles); (b) of injections, whether intramuscular, intravenous, intraarticular or subcutaneous; (c) of suppositories, both anal and vaginal; (d) anemas and vaginal douches as well as (e) catamenial and non-catamenial tampons.

Insofar as is presently known, the following brief remarks may be made about the theory underlying the utility of the amido compounds of this invention as analgesics. It will be understood that it is not intended that the invention be limited by the theory offered.

Thus, there is increased awareness nowadays of the biochemical nature of the sensation of pain. Pain results from certain prostaglandin compounds which are produced in vivo by the action of the enzyme prostaglandin synthetase upon arachidonic acid, an unsaturated fatty acid. Many traditional non-steroidal analgesics such as acetylsalicylic acid (aspirin) are believed to exert their analgesic action by the inhibition of prostaglandin synthetase activity or inactivation of prostaglandins as formed in situ or both. Thus, Norton, W. L. and Meisinger, M. A. P. state in "Inflammation", 1977, 2, No.1, pp. 37 to 46 at p. 42 that non-steroidal anti-inflammatory agents probably exert analgesic activity through prostaglandin synthesis inhibition, via a peripheral antiedema effect, a direct decrease in the pain-promoting effects of prostaglandins, or both. See generally, Wax, J., Winder, C. V., Tessman, D. K., and Stephens, M. D., 1975. "A Sensitive Method for the Comparative Bioassay of Nonsteroidal Anti-inflammatory Compounds in Adjuvant-induced Primary Inflammation in the Rat." J. Pharmacol. Exp. Ther. 192:166; Winter, C., and Flataker, L., 1965. "Nociceptive Thresholds as Affected by Parenteral Administration of Irritants and of Various Antinociceptive Drugs". J. Pharmacol. Exp. Ther. 148:373; and Collier, H. O. J., Dinneen, L. C., Johnson, C. A., and Schneider, C., 1968. "The Abdominal Constriction Response and its Suppression by Analgesic Drugs in the Mouse". Br. J. Pharmacol. Chemother. 32:295.

The unique distance of separation and spatial orientation of the two ortho substituents on a benzene ring of aspirin are believed to provide the necessary ability to inhibit the action of prostaglandin synthetase or prostaglandins themselves or both.

As stated above, the salicylamides of Formula I are known and described in existing literature. A representative, though not the only available or conceivable method of synthesis thereof is disclosed in U.S. Pat. No. 4,287,191. The succeeding description has been adopted from U.S. Pat. No. 4,287,191. In general such compounds can be prepared by reacting a lower alkyl ($R_a$) salicylate ester with an acyl chloride ($R_xCOCl$) in the presence of a Lewis acid to form an ester of a 5-acylsalicylic acid. The 5-acylsalicylic acid ester is then hydrolyzed and the resulting free acid is reacted with a substituted amine or aniline $H_2N-R_3$ to form the 5-acyl-salicylamide. The term "lower alkyl" as used herein means alkyl of from 1 through 4 carbon atoms. $R_x$ is n—$C_7$ in the case of APCF3-8 and AMCF3-8. It is n—$C_9$ in the case of AN-10. It is n—$C_8$, n—$C_9$ and n—$C_{15}$ in the cases involving ACBXE-9, ABC-4 and RV-19 respectively. In the cases of SAN-6 and S-4-F, the Friedel-Crafts acylation step is replaced by a Friedel-Crafts alkylation process by substituting the acid chloride $R_x$—CO—Cl by a normal alkyl halide $R_xCl$. In the cases of SAN-6 and S-4-F which are prepared by way of the Friedel-Crafts alkylation initial step, $R_x$ is $C_6$ and $C_4$ respectively. $R_3$ is a substituted benzene ring or a thiazole or a benzothiazole ring. In the case of a substituted benzene ring, the substituents may be —$NO_2$ in a para position or —$COOC_2H_5$ in a meta position or —$CF_3$ in either a para or a meta position. When $R_3$ is one of the two heterocyclic attachments mentioned above, the linking thereof to the secondary amido nitrogen atom occurs through the No.2 carbon atom of the heterocyclic attachment. Acryloyl AN-10 is, as already noted above, an acrylic acid derivative of AN-10 wherein the 2-hydroxy group of AN-10 is replaced by the $CH_2=CH-COO$-group. Such replacement is accomplished by the esterification of AN-10 in the manner generally employed for the esterification of phenols. Thus, esterification of AN-10 with acryloyl chloride in pyridine or other base results in the esterified product, i.e., acryloyl AN-10.

As a usual procedure, the 5-acyl or 5-alkyl salicylic acid precursor is prepared in a medium or reaction solvent which is customarily considered suitable for the conductance of a Friedel-Crafts acylation or alkylation with optimal yield, minimal side reactions, non-onerous reaction conditions and minimal reaction time. A preferred reaction solvent is carbon disulfide. Anhydrous aluminum chloride or other Lewis acid is initially added to the carbon disulfide and the mixture is cooled, e.g. with ice. A solution of the alkyl salicylate ester, e.g. methyl salicylate, and an acyl halide, e.g. a chloride (or an alkyl halide as applicable) in carbon disulfide or other reaction solvent is then slowly added and the temperature is maintained below about 10° C. After completion of reaction which may take as long as 24 hours, the reaction mass is poured into ice water and the mixture is then extracted with a suitable solvent such as ether. The ether or other extract is washed with water and then dried over anhydrous sodium sulfate. Thereafter, the ether or other solvent is evaporated in vacuo.

The resulting solid residue is dissolved in a suitable solvent such as ethanol and treated with a solution of an alkali metal hydroxide, e.g. 2N NaOH solution. After heating to a temperature of between about 80° and 120° C., e.g. on a steam bath, the mass is cooled and acidified with a suitable acid such as HCl to a pH of about 1 to precipitate the product. Recrystallization from ethanol gives purified 5-acylsalicylic acid or 5-alkylsalicylic acid, depending on whether an acid halide or an alkyl halide was the initial Friedel-Crafts reactant.

The 5-acyl or 5-alkyl salicyclic acid is reacted with the appropriate substituted aniline or other amine, e.g. p-nitroaniline in the case of AN-10, in a suitable reaction solvent such as chlorobenzene. Desirably the 5-acyl or 5-alkylsalicylic acid is pre-reacted with phosphorus trichloride in the solvent at a suitable temperature, e.g. between about 55° C. and about 80° C. The reaction time is usually between about one and about five hours. The solution is then cooled and the appropriate substituted aniline or heterocyclic amine, e.g. p-nitroaniline is then added and the solution is again heated to a suitable temperature, e.g. between about 55° C. and about 80° C. as previously described for about one to about five hours and is then refluxed until the reaction is complete, e.g. for about 24 hours. The solvent is then removed in vacuo and the residue is purified by recrystallization from a mixture of a suitable solvent such as a mixture of ethanol and water. The resulting product is an amido compound of the invention.

Detailed descriptions of the methods of synthesis of 5-n-decanoylsalicylic acid and of AN-10 therefrom are given in Examples 1 and 2 of U.S. Pat. No. 4,287,191.

Example 3 of U.S. Pat. No. 4,287,191 describes toxicity tests for AN-10 performed upon sixteen female white rats of average weight 265 gms. Example 3 concludes with the finding that $LD_{50}$ for AN-10 by the single dose oral route is greater than 2000 mg./kg. in Osborne-Mendel white rats.

Such descriptions are hereby incorporated by reference herein. Examples 1 through 3 of U.S. Pat. No. 4,287,191 are adopted as Examples 1 through 3 hereof.

Methods of synthesis of the other preferred compounds of the invention, namely APCF3-8, AMCF3-8, SAN-6, S-4-F, ACBXE-9, ABC-4 and RV-19 follow naturally from the method of synthesis described for AN-10 with appropriate substitution of the respective reactants. See generally, Batista, A. J., "Salicylanilides: Design, Synthesis, and In Vitro Evaluation as Inhibitors of Dental Plaque-Forming Microorganisms", Ph.D. Dissertation, State University of New York at Buffalo, 1980. Acryloyl AN-10 is prepared, as already noted above, from AN-10 by esterification of the phenolic —OH group of AN-10 with acryloyl chloride in pyridine.

EXAMPLES 4, 5 AND 6 AND CONTROL EXAMPLE 7

In a group of 5 male outbred hairless mice, inflammation is induced on their ears by the topical application thereto of 4.0 nmole in acetone solution (total volume 10 microliter) of the known divalent calcium ionophore (antibiotic A-23187), which is derived from *streptomyces chartreusis* and is a member of a known class of compounds having ionophoric activity. See, e.g. Pressman, B. C., "Biological Applications of Ionophores", Ann. Rev. Biochem., 45, 501, 1976. Said compound has been found, in in vivo tumor promotion studies involving topical application thereof to mice backs to have potent ability to cause skin irritation with white blood cell infiltration, erythema (skin reddening), edema, epidermal hypertrophy and subsequent epidermal hyperplasia. See Marks, F., Furstenberger, G., and Kownatzki, E., "Prostaglandin E-mediated Mitogenic Stimulation of Mouse Epidermis in vivo by divalent cation ionophore A-23187 and by tumor promoter 12-O-tetradecanoyl phorbol-13-acetate, Cancer Res., 41, 696, 1981.

In each animal only one ear is treated, the other untreated ear serving as a control.

Acute inflammation develops on treated mice ears within 4 hours following topical application of A-23187, showing both time and dose dependencies. Topical application of steroidal (hydrocortisone) and nonsteroidal (indomethacin) anti-inflammatory compositions 30 minutes after application of said ionophore causes reduction of inflammation.

In Examples 4, 5 and 6 the compounds AN-10, APCF3-8 and AMCF3-8, respectively, are topically applied to the treated ears of different groups of five male outbred hairless mice 30 minutes following the topical application thereto of the ionophore A-23187. Specifically, 1.5 micromole of the amido compound in acetone solution (total volume 10 microliters) is applied topically to treated male outbred hairless mice ears 30 min. after topical application thereto of a calcium ionophore (A-23187, 4.0 nmole total volume to 10 microliter) in acetone. As already noted, in each case, each animal serves as its own control in that only one ear is subjected to said test regime while the other ear is left untouched. Erythema and edema are assessed 4 hrs. after application of the ionophore. In Control Example 7, 3,4',5-tribromosalicylanilide (TBS) is applied in the same manner.

TBS is structurally very similar to the compounds of Formula I wherein —$R_1$ and —$R_2$ are each —Br and —$R_3$ is a parabromo substituted benzene ring.

The varying degrees of effectiveness of AN-10, APCF3-8, AMCF3-8 and TBS in the above-described tests are summarized in Table 1 below.

TABLE I

ANTI-INFLAMMATORY ACTIVITY OF SELECTED AMIDO COMPOUNDS ON INFLAMMATION OF MICE EARS CAUSED BY CALCIUM IONOPHORE (A-23187)

| Amido Compounds | Reduction in Edema (%) | Reduction in Erythema (%) |
|---|---|---|
| Example 4 AN-10 | 59 | 59 |
| Example 5 APCF3-8 | 48 | 57 |
| Example 6 AMCF3-8 | 80 | 76 |
| Control Example 7 TBS | 12 | 35 |

From the data summarized in Table 1, of the four amido compounds tested for anti-inflammatory activity, only TBS (which is not one of the compounds of the present invention) is essentially inactive at the concentration used, whereas AN-10, APCF3-8 and AMCF3-8 are all effective anti-inflammatories. Of the two isomers APCF3-8 and AMCF3-8 (which differ from each other in the position of the —$CF_3$ group), the metal isomer has a significantly higher level of activity, i.e., the meta isomer shows about 30% more edema reduction activity and about 20% more erythema reduction activity than the para isomer.

This fact is suggestive of a structure/function relationship in the inflammation reduction and/or inhibition process. Along the same lines it may be speculated as a theory underlying the mode of action of the salicylamides of Formula I, that the relative ineffectiveness of TBS is due to the decreased lipophilicity of such compound when alkyl, alkanoyl or similar —$R_1$ and —$R_2$ attachments (as already defined above) are substituted by —Br thereby leading to decreased dermal penetration.

EXAMPLES 8 THROUGH 14

Acute inflammation is induced by the application of 4 nano mole of the antibiotic A-23187 to the ears of young, male, adult hairless outbred mice (Skh:hr-1 strain). Thereafter, one of the compounds AN-10, AMCF3-8, ACBXE-9, acryloyl AN-10, S-4-F and SAN-6 is applied to the affected ears and the degree of reduction in edema (inflammation) noted.

The method used in the subject Examples differs from the method used in the preceding Examples (4 through 7) in two respects. Firstly, in the subject Examples test animals are assigned to different treatment groups in which each ear of an animal receives the same assigned treatment, i.e., the test animals of the subject Examples do not serve as their own controls as they do in the preceding four Examples.

Secondly, in the expression of the data, the objective parameter of ear weights is used as the sole data source (for the reduction of edema) as erythematous responses are not recorded. Ear weights are determined by sacrificing the animals four hours after initial application of the antibiotic A-23187 or other control material by the use of $CO_2$ gas. Thereafter, the ears are excised by cutting along the characteristic ridge readily discernible along the inner aspect of the ears. Wet and dry ear weights are used to determine the extent of the edema or inflammation present.

In Study A, 28 test animals are randomized into four treatment groups of seven each and subjected to the following ear treatment regimen:

Group A—A-23187
Group B—A-23187+AN-10
Group C—AN-10
Group D—Acetone

Each animal is dosed with a treatment consisting of a 10 microliter quantity of the assigned test material solution (or pure acetone in the case of the animals of Group D) applied to the outer aspect of both ears, i.e., 10 microliter of test material per ear. The concentrations of the respective materials in acetone solution are such that a 10 microliter dose of a solution of the antibiotic A-23187 contains 4 nano mole of such antibiotic. The corresponding quantity in the case of the AN-10 in acetone solution is 1.5 micromole. The animals of Groups A and B are initially treated with the acetone solution of A-23187. In the case of the animals of Group B alone, 10 microliter of the acetone solution of AN-10 is applied to the affected ears ½ hour after the application of the above-mentioned quantity of a solution in acetone of the antibiotic A-23187. The animals of Group C receive a 10 microliter dose per ear of the AN-10 in acetone solution alone. The animals of Group D receive a dose of 10 microliter per ear of pure acetone. All the test subjects are sacrificed four hours after the application of A-23187 to the animals of Groups A and B or the other test materials in the case of the animals of Groups C and D. The results are summarized in Table 2 noted below.

A second group of studies (Study B) is conducted on two consecutive days with two sets of mice (totalling 8 animals) received from the same shipment.

The first batch of 40 animals is divided into 80 groups of 5 each. On Day 1, the six salicylamides AN-10, AMCF3-8, ACBXE-9, acryloyl AN-10, S-4-F and SAN-6 are applied as test solutions to the untreated ears of each group of 5 animals to ascertain whether or not any of the compounds possesses inflammatory potential. The remaining two groups of 5 animals each serve as controls and their ears are dosed with A-23187 and acetone respectively. The respective quantities of the test and control materials and the methanol of administration is identical with that described for Study A. It is found that none of the six compounds being tested cause any noticeable inflammation.

On Day 2, using the second set of 40 mice, subdivided into 8 groups of 5 each, the six compounds in question are applied as acetone solutions in the manner described under Study A to mice ears inflamed with A-23187 again, as described in Study A above. As with the studies conducted on Day 1, the remaining two groups of 5 animals each serve as controls and their ears are dosed with A-23187 and acetone respectively.

The amount of each salicylamide compound applied is kept constant, for Days 1 and 2, at 1.5 micromole per 10 microliter of test solution. Sacrifice begins four hours after application A-23187, on both days, and the results are recorded. Table 2 summarizes the results of the regimen of testing involved with each one of the 30 animals in question on Day 2 with the remaining 10 animals serving as controls as already noted. Table 2 shows the reduction in edema observed with the use of each one of the six salicylamide compounds tested.

TABLE 2

| Example(s) | Compound | Reduction in Edema (%) | |
|---|---|---|---|
| | | Study A | Study B |
| 8 and 9 | AN-10 | 55 | 81 |
| 10 | Acryloyl AN-10 | * | 82 |
| 11 | AMCF3-8 | * | 81 |
| 12 | ACBXE-9 | * | 76 |
| 13 | S-4-F | * | 70 |
| 14 | SAN-6 | * | 59 |

*Not tested

Examination of the above data indicates that all six of the salicylamide compounds tested, AN-10, acryloyl AN-10, AMCF3-8, ACBXE-9, S-4-F and SAN-6 exhibit significant anti-inflammatory activity under the test conditions.

The variations noted in the activity levels for AN-10 are probably the result of individual differences between the 5 animals tested on Day 1 and the 5 animals tested on Day 2 as well as possible non-uniformity of testing conditions on the days in question. It is believed that such differences may be minimized and possibly eliminated by making use of a larger number of animals in each test group and by conducting such tests at the same time and under as uniform conditions as possible.

EXAMPLE 15

An ointment is prepared incorporating the compound AN-10 as an active ingredient. The ointment comprises the respective ingredients in the percentages shown below:

| Ingredient | wt. % |
|---|---|
| AN-10 | 1 |
| Anhydrous wool fat | 2 |
| Viscous paraffin | 10 |

-continued

| Ingredient | wt. % |
|---|---|
| White petroleum jelly | — to 100 |

AN-10 is substituted by an equivalent quantity of any one of the compounds of Formula I, e.g., APCF3-8, AMCF3-8, ACBXE-9, acryloyl AN-10, S-4-F and SAN-6 as well as mixtures thereof to form comparable ointments.

The resulting ointment is applied on the skin to relieve a painful or inflammatory condition thereof in sufficient amount to cause the spreading of 0.01 microgram to 500 microgram of the active compound per square centimeter of the dermal area affected.

The relief of pain and inflammation results. Advantageously, the ointment is applied to the affected area of the skin every four to twelve hours when pain persists.

EXAMPLE 16

An ointment of comparable efficacy to that described in Example 15 is made with the following ingredients:

| Ingredient | wt. % |
|---|---|
| Compound of Formula I | 1 |
| Cetyl alcohol | 2.4 |
| Anhydrous wool fat | 1 |
| Viscous paraffin | 15 |
| White petroleum jelly | — to 100 |

The resulting ointment is applied to the skin to relieve inflammation caused by a painful skin condition in the manner described in Example 15.

EXAMPLE 17

The compositions of this invention are also formulated into a solid form. Such forms have use as a stick-type composition intended for application to the lips or other parts of the body. Such compositions consist essentially of from 0.001% to 10%, preferably 0.01% to 5% of a compound of Formula I, e.g., acryloyl AN-10 and from 50% to 98%, preferably 60% to 90% of an emollient. This composition can further consist essentially of from 1% to 20%, preferably 5% to 15% of a suitable thickening agent, and optionally emulsifiers and water. Thickening agents include without limitation: cross-linked carboxy polymethylene polymers, methylcellulose, gum tragacanth, gum kharaya, xanthan gums and bentonite. Suitable emulsifiers are of a nonionic-anionic or cationic variety. Examples of suitable nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and difatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, glycerol, sorbitol, sorbitan, polyoxyethylene sorbitol, polyoxyethylene sorbitan, and hydrophilic wax esters. Suitable anionic emulsifiers include the fatty acid soaps, e.g., sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients noted below also have emulsifying properties.

Suitable emollients include lanolin and its derivatives namely: lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols—esters, hydrogenolysis products of lanolin, ethoxylated hydrogenated lanolin, ethoxylated sorbitol lanolin, and liquid and semi-solid lanolin absorption bases.

Additives commonly found in topical compositions such as preservatives e.g., methyl and ethyl paraben, dyes and perfume are advantageously included in any of the fore-described compositions.

An exemplary solid stick according to this invention containing one or more of the compounds of Formula I is prepared by shaping and molding the following ingredients:

| Ingredient | Wt. % |
|---|---|
| APCF3-8 | 1 |
| Carnauba wax | 40 |
| Lecithin | 40 |
| Methyl cellulose | 10 |
| Glycerol | 5 |
| Water | — to 100 |

The resulting solid stick of this Example is applied upon the skin to relieve pain or inflammation in substantially the same manner as with the ointment described in Example 15.

EXAMPLE 18

Capsules containing one or more compounds of Formula I are prepared by conventional methods. Accordingly, 300 milligrams of APCF3-8 is incorporated within the two halves of a quasi cylindrical gelatinous material which are held together with a friction fit. Said capsule halves are heat sealed for added benefit.

Said gelatinous material is alternatively substituted by a conventional non-toxic material which dissolves or disintegrates within the alimentary canal.

To capsules made according to this Example are administered orally four times daily to substantially reduce the pain associated with a painful condition of the alimentary canal, e.g., peptic ulcers and food allergies.

The foregoing list of ailments is merely illustrative and not limitative of the utility of capsules prepared according to the present invention.

EXAMPLE 19

One or more of the compounds of Formula I are also administered orally in the form of tablets.

A tablet suitable for oral administration is prepared from 300 milligrams of AMCF3-8, by the addition of 25 milligrams of starch or a water soluble gum (other pharmaceutically acceptable binding substances also being suitable) and formed into the shape of a tablet by compression within a suitable die.

The resulting tablets are administered orally for the relief of pain in the same manner as that described for the capsules of Example 18 and for the relief of pain resulting from the same conditions.

EXAMPLE 20

The compositions of this invention are also formulated in a solution form. The solution form of the composition consists essentially of from 0.001% to 10%, preferably 0.01% to 5% of a compound of Formula I, e.g., ACBXE-9 and the balance being a suitable organic solvent. Suitable organic materials useful as the solvent or a part of a solvent system are as follows: propylene glycol, glycerine, ethanol, sorbitol esters, 1,2,6-hexanetriol, isopropanol, diethyl tartrate, butanediol, and mixtures thereof. Such solvent systems can also contain water.

Accordingly, a solution is prepared as follows:

| Ingredient | Wt. % |
|---|---|
| Propylene glycol | 10 |
| Glycerine | 27 |
| ACBXE-9 | 1 |
| Ethanol | 50 |
| Water | — to 100 |

The solution is applied to the affected skin in substantially the same manner as that described for the ointment of Example 15.

EXAMPLE 21

The solution of Example 20 is incorporated in a closed metal container fitted with an aerosol cap and pressurized using conventional methods up to 100 psi. pressure with butane gas. The resulting aerosol is used as a convenient method of administering an anti-inflammatory composition of the present invention namely, one or more compounds of Formula I, e.g., ACBXE-9 for the relief of painful skin conditions. The composition of the aerosol is applied to the affected area of the skin at periodic intervals for the relief of inflammation or pain, and preferably, every four to twelve hours.

EXAMPLE 22

The compositions of this invention are also formulated in a cream form. The creams consist essentially of from 0.001% to 10%, preferably 0.01% to 5% of a compound or compounds of Formula I, e.g., S-4-F, from 5% to 50%, preferably 10% to 25% of an emollient, and the balance water. The emollients described above with respect to the compositions of the invention in a stick form (Example 17) are equally suitable herein. Optionally, the cream form contains a suitable emulsifier. The emulsifiers described in Example 17 above are also equally suitable herein. When an emulsifier is included, it is in the composition af a level from about 2% to about 10%, preferably 5%.

A cream is prepared by mixing together the following ingredients:

| Ingredient | Wt. % |
|---|---|
| S-4-F | 1 |
| Ethoxylated cholesterol | 20 |
| Sorbitol | 5 |

-continued

| Ingredient | Wt. % |
|---|---|
| Water | — to 100 |

The resulting cream is applied to the skin to relieve pain and inflammation in the same manner as that described for the ointment of Example 15.

EXAMPLE 23

A lotion is prepared incorporating one or more compounds of Formula I, e.g., SAN-6 by mixing together the following ingredients in the stated percentages on a wt/wt basis:

| Ingredient | Wt. % |
|---|---|
| SAN-6 | 1 |
| Viscous paraffin oil | 10 |
| Ethanol | 2 |
| Glycerol | 1 |
| Propylene glycol | 2 |
| Sorbic acid | 0.15 |
| Mixture of cetylstearyl alcohol and sodium cetylstearylsulfate and a non-ionic emulsifier | 0.5 |
| Perfume oil of Lily of the Valley | 0.1 |
| Water | — to 100 |

In an advantageous alternative embodiment, the above lotion contains 5 wt.% of a sun screen, e.g., para-amino benzoic acid or PABA at the expense of the water ingredient.

The resulting lotion is topically applied to relieve pain and inflammation of the skin in the same manner as that described for the cream of Example 22.

EXAMPLE 24

One or more compounds of Formula I, e.g., AN-10 are formulated into a gel form by simply admixing a suitable thickening agent with the above-described solution composition of Example 20. Examples of suitable thickening agents include: cross-linked carboxy polymethylene copolymers, methyl cellulose, gum tragacanth, gum kharaya, xanthan gums and bentonite. The gelled compositions consist essentially of from 0.001% to 10%, preferably 0.01% to 5% of a compound or compounds of Formula I, from 5% to 75% preferably 10% to 50% of an organic solvent, 0.5% to 20%, preferably 1% to 10% of the aforementioned thickening agent, the balance being water. Suitable organic solvents include without limitation glycerine, sorbitol esters, 1,2,6-hexanetriol, ethanol, isopropanol, diethyl tartrate, butanediol, and mixtures thereof.

A gel is prepared by mixing together the following ingredients:

| Ingredient | Wt. % |
|---|---|
| AN-10 | 1 |
| 1,2,6-hexanetriol | 45 |
| Bentonite | 8 |
| Water | — to 100 |

The resulting gel is applied to the skin to relieve pain or inflammation in the same manner as that described for the cream of Example 22 noted above.

EXAMPLE 25

A liniment is prepared from a gel composition of Example 24.

In the aforementioned gel composition, the presence of the bentonite thickening agent is eliminated and the balance is made up with 1,2,6-hexanetriol.

The resulting liniment is applied to the skin to relieve pain and inflammation in the same manner as that noted for the gel of Example 24.

EXAMPLE 26

One or more compounds of Formula I, e.g., AN-10 may be incorporated into solution or suspension form for the purpose of administration by way of injections, whether intravenous, intramuscular, subcutaneous, intraarticular or otherwise.

A suitable solution is prepared in an aqueous vehicle which contains the following ingredients in milligrams per milliliter of solution:

| Ingredients | Milligrams per milliliter |
|---|---|
| AN-10 | 1 |
| Isotonic sodium chloride solution | 30 |
| Dextrose | 2 |
| Invert sugar | 2 |
| Sodium lactate | 30 |
| Lactic acid | 30 |
| Water | — to 100 |

The resulting solution is suitable for administration by way of subcutaneous, intramuscular, intraarticular and intravenous administration.

Such solution is also suitable for administration to the gums by way of subcutaneous injections in preparation for dental surgery.

EXAMPLE 27

One or more of the compounds of Formula I, e.g., APCF3-8 are incorporated in an aqueous suspension for, e.g., deep intramuscular or intraarticular injection purposes.

A suitable, aqueous injectable suspension is prepared which contains the following ingredients:

| Ingredients | Milligrams per milliliter |
|---|---|
| APCF3-8 | 1 |
| Sodium citrate | 5 |
| Citric acid | 5 |
| Carboxymethylcellulose | 0.6 |
| Lecithin | 6 |
| Povidone | 0.3 |
| Methylparaben | 1 |
| Propylparaben | 0.1 |
| Sorbitan monopalmitate | 0.5 |
| Polyoxyethylene sorbitan monopalmitate | 0.5 |
| Water | — to 100 |

An intramuscular injection of about 1 to about 2 milliliters of said suspension is effective in relieving systemic pain particularly at the injection site.

An intraarticular injection of comparable quantity relieves pain in skeletal joints and surrounding areas as a result of various conditions. Non-limiting examples of such conditions include arthritis, tendonitis and rheumatism.

EXAMPLES 28 AND 29

One or more compounds of Formula I, such as AMCF3-8 is incorporated in a suppository for intraanal use.

A suppository is prepared by mixing together the following ingredients in the weight ratios shown:

| Ingredients | Percent by Weight |
|---|---|
| AMCF3-8 | 1 |
| Cocoa butter | 93 |
| Zinc oxide | 3 |
| Menthol | 2 |
| Balsam Peru | 1 |

Said suppository is prepared by melting the cocoa butter base at a temperature of about 39° C. and adding the remaining ingredients, including AMCF3-8 to the melt, with blending, to provide a homogeneous system. The cocoa butter based resulting melt is poured into molds of appropriate dimensions and allowed to solidify. The resulting product is a lubricious suppository which melts at body temperature to release the AMCF3-8 or other salicylamide compound to provide improved anti-inflammatory benefits.

Intraanal administration of the resulting suppository is effective in relieving anal pain and inflammation. The application is repeated as necessary.

A vaginal suppository is made generally following the procedure described above for making an anal suppository. The vaginal suppository has the composition noted below:

| Ingredients | Milligrams |
|---|---|
| AMCF3-8 | 1 |
| Glycerine | 5 |
| Glyceryl monopalmitate | 3 |
| Glyceryl monostearate | 3 |
| Hydrogenated palm kernel oil fatty acids | 50 |
| Hydrogenated coconut oil fatty acids | — to 100 |

In place of AMCF3-8, any one or more of the compounds of Formula I may be employed.

Intravaginal administration of the resulting suppository is effective in relieving vaginal pain and inflammation. The application is repeated as necessary.

In view of the highly anti-microbial nature of AMCF3-8 and the other compounds of Formula I, the elimination of fungal infections such as monilia is also accomplished with the use of the vaginal suppository of this Example.

Comparable benefits with respect to vaginitis are obtained with the use of said suppository.

EXAMPLE 30

An aqueous preparation containing one or more of the compounds of Formula I, such as acryloyl AN-10 is incorporated in an aqueous composition to form a douche for intravaginal administration. A composition is prepared which contains the following ingredients in the weight percentages shown below:

| Ingredients | wt. % |
|---|---|
| Acryloyl AN-10 | 1 |
| Acetic acid | 6 |
| Sodium acetate | 6 |
| Water | — to 100 |

Said composition advantageously further incorporates inert but pharmaceutically acceptable coloring matter and fragrances.

The use of the resulting composition as an intravaginal douch results in the alleviation of intravaginal pain and inflammation.

In view of the highly anti-microbial nature of the compounds of Formula I, substantial benefit with respect to bacterial infections such as monilia and vaginitis is also obtained.

EXAMPLE 31

One or more compounds of Formula I such as S-4-F is incorporated in a shampoo for application to the scalp.

A shampoo is prepared by dissolving one part by weight of S-4-F in 10 parts by weight of ethanol and incorporating the resulting solution in a shampoo base. The shampoo base contains the following ingredients:

| Ingredients | wt. % |
|---|---|
| Polyoxyethylene sorbitan monostearate | 70 |
| Triethanolamine lauryl sulfate | 10 |
| Water | 20 |

One part by weight of the S-4-F in ethanol solution is added to nine parts by weight of the above-described shampoo base to form a medicated shampoo.

Pain and inflammation of the scalp is effectively alleviated by the use of such shampoo with repeat applications as needed.

EXAMPLE 32

Soaps containing one or more of the compounds of Formula I are prepared as a further vehicle for the topical administration of said compounds.

A commercially available bar of soap consisting of a predominant quantity of the sodium or potassium salts of various fatty acids or of alkali metal isethionates is melted with mild heating.

To 99 parts by weight of the melted soap, one part by weight of SAN-6 is added with stirring.

Said soap and SAN-6 mixture is thereafter made into soap bars by any of the conventional methods employed for that purpose including, e.g., extrusion into the form of a rod, followed by cutting into billets and the stamping of the resulting billets into tablets of soap. Alternatively, the molten soap and SAN-6 mixture may simply be poured into molds and permitted to solidify.

The resulting medicated soap is used in the washing of affected areas of the skin or for general purpose bathing to bring about relief of pain and inflammation of the skin.

The use of such soap is also beneficial in preventing or eliminating acne and infections of the skin in view of the highly anti-microbial nature of the compounds of Formula I.

EXAMPLE 33

The compounds of Formula I are incorporated in a suitable lubricating base to form an enema.

An enema is prepared by the incorporation of a 10% solution in ethanol of AN-10 is a castor oil base. The ratio of the ethanol solution to castor oil is 1:9.

The administration of one to ten milliliters of the resulting composition by way of an intraanal syringe results in the relief of rectal pain.

EXAMPLES 34, 35 and 36

Medicated ear drops containing one or more of the compounds of Formula I such as AN-10 are prepared by the mixing together of the following ingredients in the parts by weight noted below:

| Ingredient | wt. % |
| --- | --- |
| AN-10 | 1 |
| Triethanolamine polypeptide oleate-condensate | 10 |
| Chlorbutanol | 0.5 |
| Propylene glycol | — to 100 |

The administration of the resulting ear drops into the ear cavity or auditory canal, with repeated applications as needed, results in the relief of painful conditions of the ear, included but not limited to, pain which is solely the result of dermal inflammation.

Nose drops containing one or more of the compounds of Formula I such as APCF3-8 are prepared by mixing such compound together with the other ingredients in the proportions noted below:

| Ingredient | wt. % |
| --- | --- |
| APCF3-8 | 1 |
| Essential oil of cajeput | 0.5 |
| Essential oil of eucalyptus | 0.5 |
| Essential oil of peppermint | 0.5 |
| Cottonseed oil | — to 100 |

Administration of three to four drops in each nostril of nose drops of the composition noted above three to four times daily results in the relief of pain and inflammation of skin and the nasal mucous membranes.

The composition described above may alternatively be incorporated into a compressed air nebulizer and administered in like manner with equal efficacy.

Eye drops containing one or more of the compound of Formula I such as ACBXE-9 are prepared by mixing together the following ingredients in the proportions noted below:

| Ingredient | wt. % |
| --- | --- |
| ACBXE-9 | 1 |
| Ethyl alcohol | 0.5 |
| Thimerosal (preservative) | 0.001 |
| Propylene glycol | 10 |
| Sodium chloride | 3 |
| Water | — to 100 |

The application of one or two drops of eye drops of the above composition, repeated as required, is effective in reducing and eliminating pain and inflammation. In view of the anti-microbial properties of the compounds of Formula I, eye infections are also effectively abated or prevented.

EXAMPLES 37 AND 38

Medicated sanitary napkins, medicated pads and medicated dressings are prepared by the incorporation of one or more of the compounds of Formula I in a suitable cotton wool or other absorbent article.

A sanitary napkin is prepared in accordance with the method described in Example 3 of U.S. Pat. No. 4,226,237.

The resulting sanitary napkin is sprayed with a 10% wt./wt. acryloyl AN-10 in acetone solution to insure a concentration spread of 0.01 gram AN-10 per square centimeter of the napkin. After drying in an aerated chamber at room temperature the napkin is hermetically sealed in a polyethylene or metal foil envelope.

The resulting pad is effective in relieving pain and inflammation when used as a medicated pad.

A pad is prepared in a size other than that to which the teachings of U.S. Pat. No. 4,226,237 are confined to thereby produce a medicated pad or a medicated dressing for use in the bandaging of wounds, lacerations, and other conditions of the skin which cause pain.

The resulting pads and dressings when made of selected differing dimensions are effective in relieving pain and inflammation when used as medicated pads and as medicated dressings.

EXAMPLE 39 AND 40

One or more compounds of Formula I, such as acryloyl AN-10 are incorporated in plasters and bandages.

To this purpose, a plaster or a bandage is sprinkled with a 10% wt./wt. acryloyl AN-10 in acetone solution to the extent of 0.01 gram acryloyl AN-10 per square centimeter of surface area. Following drying in an aerated chamber at room temperature, the resulting plasters and bandages are stored in hermetically sealed polyethylene or metal foil envelopes to prevent loss of the salicylamide compound from the medicated plaster or medicated bandage.

The term plaster as used herein means a wound dressing which has an adhesive coated on one side thereof. Advantageously, the adhesive material is one which is not affected by the acryloyl AN-10 in acetone solution. The term bandage as used herein means a roll of cotton or other fabric of sterile nature without the incorporation therein of an adhesive which is used in the dressing of wounds.

The acryloyl AN-10 impregnated plaster or bandage is used with enhanced, therapeutic value when utilized in the dressing of wounds by minimizing or eliminating the pain associated with wounds, lacerations, inflammation and like conditions.

EXAMPLES 41 AND 42

One or more of the compounds of Formula I, such as S-4-F are incorporated in a catamenial or non-catamenial tampon.

A catamenial tampon is prepared in accordance with the method described in U.S. Pat. No. 4,226,237, of the kind shown in the illustrative embodiments included in FIGS. 8 and 10 thereof.

The outer surface of said catamenial tampon is sprinkled with a 10% wt./wt. acetone solution of S-4-F in an amount sufficient to provide a concentration of 0.01 gram of such compound per square centimeter of the outer surface of such tampon. Following drying in an aerated chamber at room temperature, the tampon is stored in a sealed polyethylene or metal foil pouch, in order to guard against the loss of any S-4-F compound prior to the use of such tampon.

When the resulting catamenial tampon is intravaginally worn, relief of intravaginal pain and inflammation is noticed. Additionally, in view of the highly antimicrobial nature of the compounds of Formula I, including S-4F, bacterial conditions such as monilia are effectively combated and prevented.

When said tampon is prepared in appropriate (smaller) dimensions, such as to enable the same to fit snugly within other body cavities such as the ears and the nose without causing any discomfort to the wearer, similar relief from pain and inflammation of skin as well as affected mucous membranes is noticed. As an added benefit the effective combating or elimination of microbial infections is also noticed as a result of the highly anti-microbial nature of compounds of Formula I.

As will be readily apparent to persons of ordinary skill in the art to which the present invention pertains, various modifications of such invention as hereinbefore set forth and as further defined in the appended claims may be made without departing from the spirit and scope thereof regardless of the applicability of the theoretical bases advanced herein in elucidation of the invention.

What is claimed is:

1. A medicated pad comprising a pad and, carried on said pad, an admixture of a pharmaceutically acceptable carrier and an anti-inflammatorily effective amount of an anti-inflammatory compound of the formula:

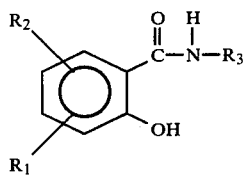

wherein the lipophilicity imparting substituents —$R_1$ and —$R_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —$R_1$ and —$R_2$ substituents comprising up to about 30 carbon atoms when taken together either attached directly to the phenyl ring provided with an amido and a hydroxyl group in an ortho orientation with respect to each other or attached to said phenyl ring through a

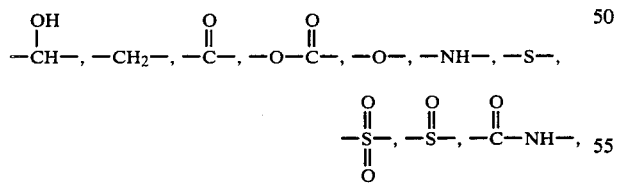

—NH—CH$_2$— or

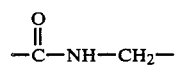

group with the proviso that —$R_1$ and —$R_2$ are not both —H and wherein —$R_3$ is selected from the group consisting of thiazol-2-yl, benzothiazol-2-yl and $R_4$-substituted phenyl wherein $R_4$ is selected from the group consisting of —OH, —COOH, the tautomeric pair

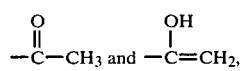

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$, wherein X$_1$, X$_2$ and X$_3$ are halogen atoms.

2. A medicated pad comprising a pad and, carried on said pad, an admixture of a pharmaceutically acceptable vehicle and an analgesically effective amount of an analgesic compound of the formula:

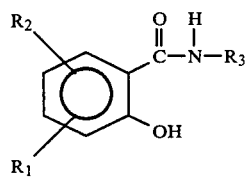

wherein the lipophilicity imparting substituents —$R_1$ and —$R_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —$R_1$ and —$R_2$ substituents comprising up to about 30 carbon atoms when taken together either attached directly to the phenyl ring provided with an amido and a hydroxyl group in an ortho orientation with respect to each other or attached to said phenyl ring through a

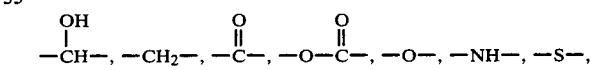

—NH—CH$_2$— or

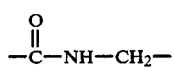

group with the proviso that —$R_1$ and —$R_2$ are not both —H and wherein —$R_3$ is selected from the group consisting of thiazol-2-yl, benzothiazol-2-yl and $R_4$-substituted-phenyl wherein $R_4$ is selected from the group consisting of —OH, —COOH, the tautomeric pair

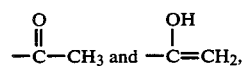

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

3. A medicated pad according to claim 1 or claim 2 wherein —$R_3$ is of the form —CH$_2$—$R_6$ wherein —$R_6$ is a C$_1$ to C$_{24}$ attachment of the same description as —$R_1$ and —$R_2$.

4. A medicated pad according to claim 1 or claim 2 wherein X$_1$, X$_2$ and X$_3$ are identical halogen atoms.

5. A medicated pad according to claim 4 wherein $X_1$, $X_2$ and $X_3$ are fluorine atoms.

6. A medicated pad according to claim 1 or 2 wherein $R_3$ is $R_4$-substituted-phenyl and $R_4$ is selected from the group consisting of $-NO_2$ and $-CF_3$.

7. A medicated pad according to claim 6 wherein $R_4$ is meta-$CF_3$.

8. A medicated pad according to claim 6 wherein $R_4$ is in the para position.

9. A medicated pad according to claim 1 or claim 2 wherein the compound is selected from the group consisting of a compound of the formula:

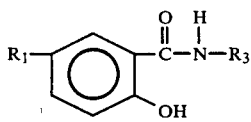

wherein;
(a) $R_1$ is n-decanoyl, Y is hydroxy and $R_3$ is p-nitrophenyl;
(b) $R_1$ is n-octanoyl, Y is hydroxy and $R_3$ is p-trifluoromethylphenyl;
(c) $R_1$ is n-octanoyl, Y is hydroxy and $R_3$ is m-trifluoromethylphenyl;
(d) $R_1$ is n-hexyl, Y is hydroxy and $R_3$ is p-nitrophenyl;
(e) $R_1$ is n-butyl, Y is hydroxy and $R_3$ is m-trifluoromethylphenyl;
(f) $R_1$ is n-nonanoyl, Y is hydroxy and $R_3$ is m-carbethoxyphenyl;
(g) $R_1$ is n-decanoyl, Y is hydroxy and $R_3$ is benzothiazol-2-yl;
(h) $R_1$ is n-hexadecanoyl, Y is hydroxy and $R_3$ is thiazol-2-yl;
(i) $R_1$ is n-decanoyl, Y is acryloyloxy and $R_3$ is p-nitrophenyl;
and mixtures thereof.

10. A medicated plaster comprising a plaster and, carried on said plaster, an admixture of a pharmaceutically acceptable carrier vehicle an anti-inflammatorily effective amount of an anti-inflammatory compound of the formula:

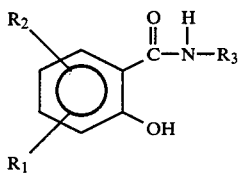

wherein the lipophilicity imparting substituents $-R_1$ and $-R_2$ which impart an octanol/water distribution function of about 4.5 to about 10 to said compound are $-H$, normal or branched chain or cyclic or fused ring polycyclic or non-fused ring polycyclic alkyl, alkenyl, alkynyl, aryl or heteroaryl groups optionally containing further substituents thereon, said $-R_1$ and $-R_2$ substituents comprising up to about 30 carbon atoms when taken together either attached directly to the phenyl ring provided with an amido and a hydroxyl group in an ortho orientation with respect to each other or attached to said phenyl ring through a

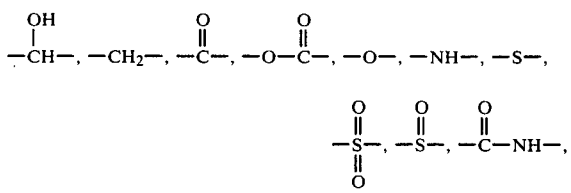

$-NH-CH_2-$ or

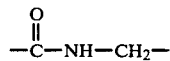

group with the proviso that $-R_1$ and $-R_2$ are not both $-H$ and wherein $-R_3$ is selected from the group consisting of thiazol-2-yl, benzothiazol-2-yl and $R_4$-substituted phenyl wherein $R_4$ is selected from the group consisting of $-OH$, $-COOH$, the tautomeric pair

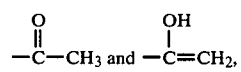

$-CH_2COOH$, $-COOCH_3$, $-COOC_2H_5$, $-CH_2COOCH_3$, $-CH_2COOC_2H_5$, $-NO_2$, and $CX_1X_2X_3$ wherein $X_1$, $X_2$ and $X_3$ are halogen atoms.

11. A medicated plaster comprising a plaster and, carried on said plaster, an admixture of a pharmaceutically acceptable carrier vehicle and an analgesically effective amount of an analgesic compound of the formula:

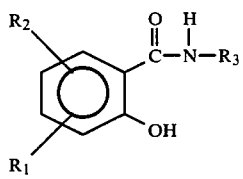

wherein the lipophilicity imparting substituents $-R_1$ and $-R_2$ which impart an octanol/water distribution function of about 4.5 to about 10 to said compound are $-H$, normal or branched chain or cyclic or fused ring polycyclic or non-fused ring polycyclic alkyl, alkenyl, alkynyl, aryl or heteroaryl groups optionally containing further substituents thereon, said $-R_1$ and $-R_2$ substituents comprising up to about 30 carbon atoms when taken together either attached directly to the phenyl ring provided with an amido and a hydroxyl group in an ortho orientation with respect to each other or attached to said phenyl ring through a

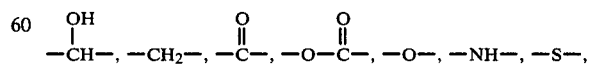

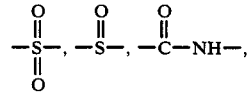

$-NH-CH_2-$ or

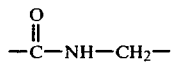

group with the proviso that —R$_1$ and —R$_2$ are not both —H and wherein —R$_3$ is selected from the group consisting of thiazol-2-yl, benzothiazol-2-yl and R$_4$-substituted-phenyl wherein R$_4$ is selected from the group consisting of —OH, —COOH, the tautomeric pair

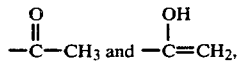

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

12. A medicated plaster according to claim 10 or claim 11 wherein —R$_3$ is of the form —CH$_2$—R$_6$ wherein —R$_6$ is a C$_1$ to C$_{24}$ attachment of the same description as —R$_1$ and —R$_2$.

13. A medicated plaster according to claim 10 or claim 11 wherein X$_1$, X$_2$ and X$_3$ are identical halogen atoms.

14. A medicated plaster according to claim 13 wherein X$_1$, X$_2$ and X$_3$ are fluorine atoms.

15. A medicated plaster according to claim 10 or claim 11 wherein —R$_3$ is R$_4$-substituted-phenyl and R$_4$ is selected from the group consisting of —NO$_2$ and —CF$_3$.

16. A medicated plaster according to claim 15 wherein R$_4$ is meta-CF$_3$.

17. A medicated plaster according to claim 15 wherein R$_4$ is in the para position.

18. A medicated plaster according to claim 10 or claim 11 wherein the compound is selected from the group consisting of a compound of the formula:

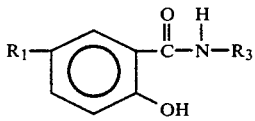

wherein;
(a) R$_1$ is n-decanoyl, Y is hydroxy and R$_3$ is p-nitrophenyl;
(b) R$_1$ is n-octanoyl, Y is hydroxy and R$_3$ is p-trifluoromethylphenyl;
(c) R$_1$ is n-octanoyl, Y is hydroxy and R$_3$ is m-trifluoromethylphenyl;
(d) R$_1$ is n-hexyl, Y is hydroxy and R$_3$ is p-nitrophenyl;
(e) R$_1$ is n-butyl, Y is hydroxy and R$_3$ is m-trifluoromethylphenyl;
(f) R$_1$ is n-nonanoyl, Y is hydroxy and R$_3$ is m-carbethoxyphenyl;
(g) R$_1$ is n-decanoyl, Y is hydroxy and R$_3$ is benzothiazol-2-yl;
(h) R$_1$ is n-hexadecanoyl, Y is hydroxy and R$_3$ is thiazol-2-yl;
(i) R$_1$ is n-decanoyl, Y is acryloyloxy and R$_3$ is p-nitrophenyl;
and mixtures thereof.

19. A medicated bandage or medicated dressing comprising a bandage or a dressing and, carried on said bandage or said dressing, an admixture of a pharmaceutically acceptable carrier vehicle and an anti-inflammatorily effective amount of an anti-inflammatory compound of the formula:

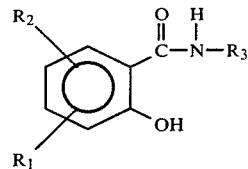

wherein the lipophilicity imparting substituents —R$_1$ and —R$_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —R$_1$ and —R$_2$ substituents comprising up to about 30 carbon atoms when taken together either attached directly to the phenyl ring provided with an amido and a hydroxyl group in an ortho orientation with respect to each other or attached to said phenyl ring through a

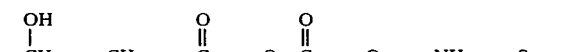

—NH—CH$_2$— or

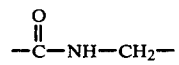

group with the proviso that —R$_1$ and —R$_2$ are not both —H and wherein —R$_3$ is selected from the group consisting of thiazol-2-yl, benzothiazol-2-yl and R$_4$-substituted phenyl wherein R$_4$ is selected from the group consisting of —OH, —COOH, the tautomeric pair

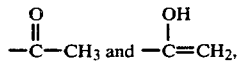

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

20. A medicated bandage or medicated dressing comprising a bandage or a dressing and, carried on said bandage or said dressing, an admixture of a pharmaceutically acceptable carrier vehicle and an analgesically effective amount of an analgesic compound of the formula:

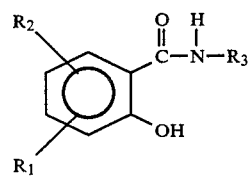

wherein the lipophilicity imparting substituents —R$_1$ and —R$_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or hetroaryl groups optionally containing further substituents thereon, said —R₁ and —R₂ substituents comprising up to about 30 carbon atoms when taken together either attached directly to the phenyl ring provided with an amido and a hydroxyl group in an ortho orientation with respect to each other or attached to said phenyl ring through a

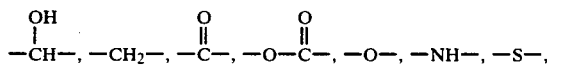

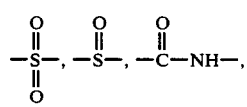

—NH—CH₂— or

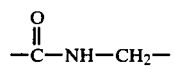

group with the proviso that —R₁ and —R₂ are not both —H and wherein —R₃ is selected from the group consisting of thiazol-2-yl, benzothiazol-2-yl and R₄-substituted-phenyl wherein R₄ is selected from the group consisting of —OH, —COOH, the tautomeric pair

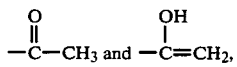

—CH₂COOH, —COOCH₃, —COOC₂H₅, —CH₂COOCH₃, —CH₂COOC₂H₅, —NO₂, and CX₁X₂X₃ wherein X₁, X₂ and X₃ are halogen atoms.

21. A medicated bandage or medicated dressing according to claim 19 or claim 20 wherein —R₃ is of the form —CH₂—R₆ wherein —R₆ is a C₁ to C₂₄ attachment of the same description as —R₁ and —R₂.

22. A medicated bandage or medicated dressing according to claim 19 or claim 20 wherein X₁, X₂ and X₃ are identical halogen atoms.

23. A medicated bandage or medicated dressing according to claim 22 wherein X₁, X₂ and X₃ are fluorine atoms.

24. A medicated bandage or medicated dressing according to claim 19 or 20 wherein R₃ is R₄-substituted-phenyl and R₄ is selected from the group consisting of —NO₂ and —CF₃.

25. A medicated bandage or medicated dressing according to claim 24 wherein R₄ is meta-CF₃.

26. A medicated bandage or medicated dressing according to claim 24 wherein R₄ is in the para position.

27. A medicated bandage or medicated dressing according to claim 19 or claim 20 wherein the compound is selected from the group consisting of a compound of the formula:

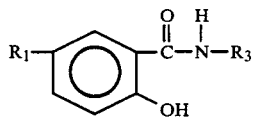

wherein;

(a) R₁ is n-decanoyl, Y is hydroxy and R₃ is p-nitrophenyl;

(b) R₁ is n-octanoyl, Y is hydroxy and R₃ is p-trifluoromethylphenyl;

(c) R₁ is n-octanoyl, Y is hydroxy and R₃ is m-trifluoromethylphenyl;

(d) R₁ is n-hexyl, Y is hydroxy and R₃ is p-nitrophenyl;

(e) R₁ is n-butyl, Y is hydroxy and R₃ is m-trifluoromethylphenyl;

(f) R₁ is n-nonanoyl, Y is hydroxy and R₃ is m-carbethoxyphenyl;

(g) R₁ is n-decanoyl, Y is hydroxy and R₃ is benzothiazol-2-yl;

(h) R₁ is n-hexadecanoyl, Y is hydroxy and R₃ is thiazol-2-yl;

(i) R₁ is n-decanoyl, Y is acryloyloxy and R₃ is p-nitrophenyl;

and mixtures thereof.

28. A medicated catamenial tampon comprising a catamenial tampon and, carried on said catamenial tampon, an admixture of a pharmaceutically acceptable carrier vehicle and an anti-inflammatorily effective amount of an anti-inflammatory compound of the formula:

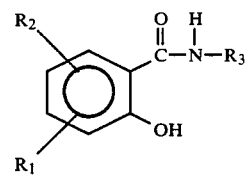

wherein the lipophilicity imparting substituents —R₁ and —R₂ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —R₁ and —R₂ substituents comprising up to about 30 carbon atoms when taken together either attached directly to the phenyl ring provided with an amido and a hydroxyl group in an ortho orientation with respect to each other or attached to said phenyl ring through a

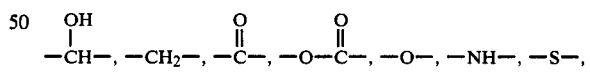

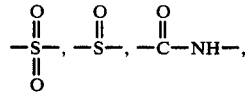

—NH—CH₂— or

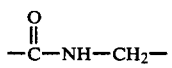

group with the proviso that —R₁ and —R₂ are not both —H and wherein —R₃ is selected from the group consisting of thiazol-2-yl, benzothiazol-2-yl and R₄-substituted phenyl wherein R₄ is selected from the group consisting of —OH, —COOH, the tautomeric pair

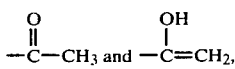

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

29. A medicated catamenial tampon comprising a catamenial tampon and, carried on said catamenial tampon, an admixture of a pharmaceutically effective carrier vehicle and an analgesically effective amount of an analgesic compound of the formula:

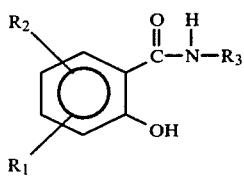

wherein the lipophilicity imparting substituents —R$_1$ and —R$_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —R$_1$ and —R$_2$ substituents comprising up to about 30 carbon atoms when taken together either attached directly to the phenyl ring provided with an amido and a hydroxyl group in an ortho orientation with respect to each other or attached to said phenyl ring through a

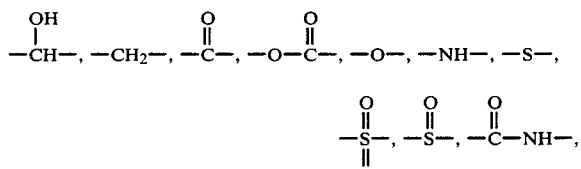

—NH—CH$_2$— or

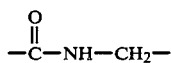

group with the proviso that —R$_1$ and —R$_2$ are not both —H and wherein —R$_3$ is selected from the group consisting of thiazol-2-yl, benzothiazol-2-yl and R$_4$-substituted phenyl wherein R$_4$ is selected from the group consisting of —OH, —COOH, the tautomeric pair

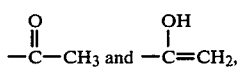

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

30. A medicated catamenial tampon according to claim 28 or claim 29 wherein —R$_3$ is of the form —CH$_2$—R$_6$ wherein —R$_6$ is a C$_1$ to C$_{24}$ attachment of the same description as —R$_1$ and —R$_2$.

31. A medicated catamenial tampon according to claim 28 or claim 29 wherein X$_1$, X$_2$ and X$_3$ are identical halogen atoms.

32. A medicated catamenial tampon according to claim 31 wherein X$_1$, X$_2$ and X$_3$ are fluorine atoms.

33. A medicated catamenial tampon according to claim 28 or claim 29 wherein R$_3$ is R$_4$-substituted-phenyl and R$_4$ is selected from the group consisting of —NO$_2$ and —CF$_3$.

34. A medicated catamenial tampon according to claim 33 wherein R$_4$ is meta-CF$_3$.

35. A medicated catamenial tampon according to claim 33 wherein R$_4$ is in the para position.

36. A medicated catamenial tampon according to claim 18 or claim 19 wherein the compound is selected from the group consisting of a compound of the formula:

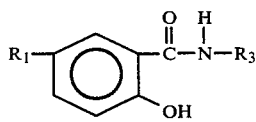

wherein;
(a) R$_1$ is n-decanoyl, Y is hydroxy and R$_3$ is p-nitrophenyl;
(b) R$_1$ is n-octanoyl, Y is hydroxy and R$_3$ is p-trifluoromethylphenyl;
(c) R$_1$ is n-octanoyl, Y is hydroxy and R$_3$ is m-trifluoromethylphenyl;
(d) R$_1$ is n-hexyl, Y is hydroxy and R$_3$ is p-nitrophenyl;
(e) R$_1$ is n-butyl, Y is hydroxy and R$_3$ is m-trifluoromethylphenyl;
(f) R$_1$ is n-nonanoyl, Y is hydroxy and R$_3$ is m-carbethoxyphenyl;
(g) R$_1$ is n-decanoyl, Y is hydroxy and R$_3$ is benzothiazol-2-yl;
(h) R$_1$ is n-hexadecanoyl, Y is hydroxy and R$_3$ is thiazol-2-yl;
(i) R$_1$ is n-decanoyl, Y is acryloyloxy and R$_3$ is p-nitrophenyl;
and mixtures thereof.

37. A medicated non-catamenial tampon comprising a non-catamenial tampon and, carried on said non-catamenial tampon, an admixture of a pharmaceutically acceptable carrier vehicle and an anti-inflammatorily effective amount of an anti-inflammatory compound of the formula:

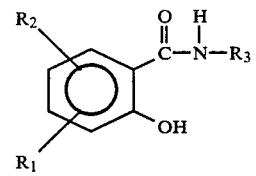

wherein the lipophilicity imparting substituents —R$_1$ and —R$_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —R$_1$ and —R$_2$ substituents comprising up to about 30 carbon atoms when taken together either attached directly to the phenyl ring provided with an amido and a hydroxyl group in an ortho orientation with respect to each other or attached to said phenyl ring through a

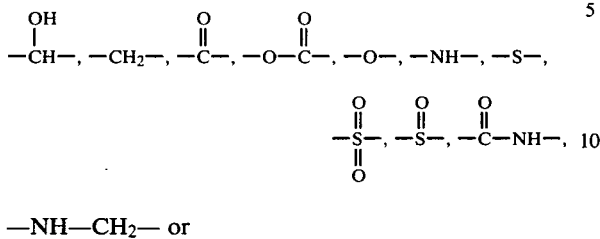

—NH—CH$_2$— or

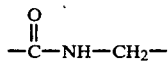

group with the proviso that —R$_1$ and —R$_2$ are not both —H and wherein —R$_3$ is selected from the group consisting of thiazol-2-yl, benzothiazol-2-yl and R$_4$-substituted phenyl wherein R$_4$ is selected from the group consisting of —OH, —COOH, the tautomeric pair

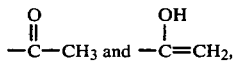

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

38. A medicated non-catamenial tampon comprising a non-catamenial tampon and, carried on said non-catamenial tampon, an admixture of a pharmaceutically acceptable carrier vehicle and an analgesically effective amount of an analgesic compound of the formula:

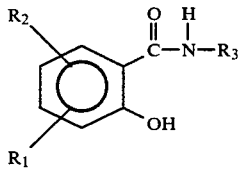

wherein the lipophilicity imparting substituents —R$_1$ and —R$_2$ which impart an octanol/water distribution function of about 4.5 to about 10 to said compound are —H, normal or branched chain or cyclic or fused ring polycyclic or non-fused ring polycyclic alkyl, alkenyl, alkynyl, aryl or heteroaryl groups optionally containing further substituents thereon, said —R$_1$ and —R$_2$ substituents comprising up to about 30 carbon atoms when taken together either attached directly to the phenyl ring provided with an amido and a hydroxyl group in an ortho orientation with respect to each other or attached to said phenyl ring through a

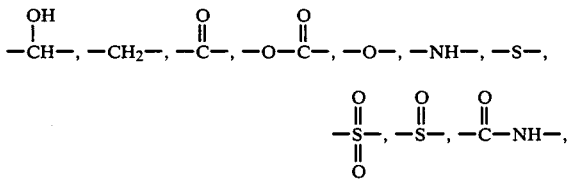

—NH—CH$_2$— or

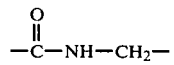

group with the proviso that —R$_1$ and —R$_2$ are not both —H and wherein —R$_3$ is selected from the group consisting of thiazol-2-yl, benzothiazol-2-yl and R$_4$-substituted phenyl wherein R$_4$ is selected from the group consisting of —OH, —COOH, the tautomeric pair

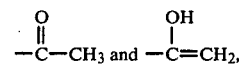

—CH$_2$COOH, —COOCH$_3$, —COOC$_2$H$_5$, —CH$_2$COOCH$_3$, —CH$_2$COOC$_2$H$_5$, —NO$_2$, and CX$_1$X$_2$X$_3$ wherein X$_1$, X$_2$ and X$_3$ are halogen atoms.

39. A medicated non-catamenial tampon according to claim 37 or claim 38 wherein —R$_3$ is of the form —CH$_2$—R$_6$ wherein —R$_6$ is a C$_1$ to C$_{24}$ attachment of the same desceiption as —R$_1$ and —R$_2$.

40. A medicated non-catamenial tampon according to claim 37 or claim 38 wherein X$_1$, X$_2$ and X$_3$ are identical halogen atoms.

41. A medicated non-catamenial tampon according to claim 40 wherein X$_1$, X$_2$ and X$_3$ are fluorine atoms.

42. A medicated non-catamenial tampon according to claim 37 or claim 38 wherein R$_3$ is R$_4$-substituted-phenyl and R$_4$ is selected from the group consisting of —NO$_2$ and —C$_3$.

43. A medicated non-catamenial tampon according to claim 42 wherein R$_4$ is meta-C$_3$.

44. A medicated non-catamenial tampon according to claim 42 wherein R$_4$ is in the para position.

45. A medicated non-catamenial tampon according to claim 37 or claim 38 wherein the compound is selected from the group consisting of a compound of the formula:

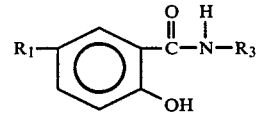

wherein;
(a) R$_1$ is n-decanoyl, Y is hydroxy and R$_3$ is p-nitrophenyl;
(b) R$_1$ is n-octanoyl, Y is hydroxy and R$_3$ is p-trifluoromethylphenyl;
(c) R$_1$ is n-octanoyl, Y is hydroxy and R$_3$ is m-trifluoromethylphenyl;
(d) R$_1$ is n-hexyl, Y is hydroxy and R$_3$ is p-nitrophenyl;
(e) R$_1$ is n-butyl, Y is hydroxy and R$_3$ is m-trifluoromethylphenyl;
(f) R$_1$ is n-nonanoyl, Y is hydroxy and R$_3$ is m-carbethoxyphenyl;
(g) R$_1$ is n-decanoyl, Y is hydroxy and R$_3$ is benzothiazol-2-yl;
(h) R$_1$ is n-hexadecanoyl, Y is hydroxy and R$_3$ is thiazol-2-yl;
(i) R$_1$ is n-decanoyl, Y is acryloyloxy and R$_3$ is p-nitrophenyl;
and mixtures thereof.

* * * * *